(12) United States Patent
Aeby et al.

(10) Patent No.: US 10,039,701 B2
(45) Date of Patent: Aug. 7, 2018

(54) PERMANENT HAIR COLORANTS BASED ON A CREAM-LIKE CARRIER AND A COMBINATION OF TRIS(HYDROXYMETHYL) AMINOMETHANE, AT LEAST AN AMINO ACID AND AN OXIDATIVE DYE

(71) Applicant: HCT—Hair Cosmetic Technology AG, Marly (CH)

(72) Inventors: Johann Aeby, Marly (CH); Otto Richard Gottel, Marly (CH)

(73) Assignee: HCT—Hair Cosmetic Technology AG, Marly (CH)

( * ) Notice: Subject to any disclaimer, the term of this patent is extended or adjusted under 35 U.S.C. 154(b) by 0 days.

(21) Appl. No.: 15/500,455

(22) PCT Filed: Jul. 24, 2015

(86) PCT No.: PCT/EP2015/067067
§ 371 (c)(1),
(2) Date: Jan. 30, 2017

(87) PCT Pub. No.: WO2016/016148
PCT Pub. Date: Feb. 4, 2016

(65) Prior Publication Data
US 2017/0216174 A1    Aug. 3, 2017

(30) Foreign Application Priority Data
Jul. 30, 2014 (EP) .................................... 14179192

(51) Int. Cl.
*A61Q 5/10* (2006.01)
*A61K 8/41* (2006.01)
(Continued)

(52) U.S. Cl.
CPC ................ *A61K 8/41* (2013.01); *A61K 8/22* (2013.01); *A61K 8/347* (2013.01); *A61K 8/411* (2013.01);
(Continued)

(58) Field of Classification Search
CPC ... A61K 8/41; A61K 8/44; A61K 8/55; A61K 8/556; A61K 8/22; A61K 8/411;
(Continued)

(56) References Cited

U.S. PATENT DOCUMENTS

2008/0219937 A1* 9/2008 Msika ................ A61K 8/4973
424/59

FOREIGN PATENT DOCUMENTS

| EP | 2143414 A2 | 1/2010 |
| GB | 2506692 A | 4/2014 |

OTHER PUBLICATIONS

European Patent Office, International Search Report, dated Aug. 25, 2015.
(Continued)

*Primary Examiner* — Eisa B Elhilo
(74) *Attorney, Agent, or Firm* — Ice Miller LLP

(57) ABSTRACT

The present invention relates to a cosmetic composition, preferably for keratin fibers such as compositions for coloring hair, comprising at least these components: a. tris (hydroxymethyl)aminomethane; b. at least one amino acid; c. at least one organic phosphate ester compound selected from: c1. monoester of phosphates of alkoxylated fatty alcohols, wherein the alkoxylated fatty alcohols are composed of C12-C22 fatty alcohols alkoxylated with from 1 to 50 moles of an alkylene oxide, wherein the number of moles of alkylene oxide is with respect to the moles of fatty alcohol; c2. diester of phosphates of non-alkoxylated fatty alcohols, wherein the non-alkoxylated fatty alcohols are
(Continued)

composed of C12-C22 fatty alcohols; and c3. mixtures of c1 and c2; d. water; the present invention further refers to a process of manufacturing a dispersion comprising the aforementioned cosmetic composition; a kit of two or more components for coloring keratin fibers; a ready-to-use composition obtainable by mixing the kit components; and a process for coloring keratin fibers comprising said ready-to-use composition.

19 Claims, 2 Drawing Sheets

(51) Int. Cl.
| | |
|---|---|
| *A61K 8/44* | (2006.01) |
| *A61K 8/55* | (2006.01) |
| *A61Q 5/08* | (2006.01) |
| *A61K 8/34* | (2006.01) |
| *A61K 8/22* | (2006.01) |

(52) U.S. Cl.
CPC .................. *A61K 8/44* (2013.01); *A61K 8/55* (2013.01); *A61K 8/556* (2013.01); *A61Q 5/08* (2013.01); *A61Q 5/10* (2013.01); *A61K 2800/4324* (2013.01); *A61K 2800/88* (2013.01)

(58) Field of Classification Search
CPC ................ A61K 8/347; A61K 2800/88; A61K 2800/4324; A61Q 5/10; A61Q 5/08
See application file for complete search history.

(56) References Cited

OTHER PUBLICATIONS

European Patent Office, Written Opinion of the International Searching Authority, dated Aug. 25, 2015.

* cited by examiner

PERMANENT HAIR COLORANTS BASED ON A CREAM-LIKE CARRIER AND A COMBINATION OF TRIS(HYDROXYMETHYL) AMINOMETHANE, AT LEAST AN AMINO ACID AND AN OXIDATIVE DYE

CROSS-REFERENCE TO RELATED APPLICATIONS

The present application is a U.S. national stage of, and claims the priority benefit of, International Patent Application Serial No. PCT/EP2015/067067, filed Jul. 24, 2015 and also claims the priority benefit of European Patent Application Serial No. 14179192.1, filed Jul. 30, 2014, the text and drawings of which are hereby incorporated by reference in their entireties.

The present invention relates to a cosmetic composition, preferably for keratin fibers such as compositions for coloring hair, comprising at least these components: a. tris (hydroxymethyl)aminomethane; b. at least one amino acid; c. at least one organic phosphate ester compound selected from: c1. monoester of phosphates of alkoxylated fatty alcohols, wherein the alkoxylated fatty alcohols are composed of C12-C22 fatty alcohols alkoxylated with from 1 to 50 moles of an alkylene oxide, wherein the number of moles of alkylene oxide is with respect to the moles of fatty alcohol; c2. diester of phosphates of non-alkoxylated fatty alcohols, wherein the non-alkoxylated fatty alcohols are composed of C12-C22 fatty alcohols; and c3. mixtures of c1 and c2; d. water; the present invention further refers to a process of manufacturing a dispersion comprising the aforementioned cosmetic composition; a kit of two or more components for coloring keratin fibers; a ready-to-use composition obtainable by mixing the kit components; and a process for coloring keratin fibers comprising said ready-to-use composition.

Cosmetic compositions based on oxidative dyes play an important role in coloring keratin fibers, in particular of human hair, because of their intensive coloring and advantageous long-term color stability. Such cosmetic compositions normally comprise one or more precursors of oxidative dyes, so-called primary intermediates, and one or more color coupling agents. Compositions comprising primary intermediates and couplers are activated with an oxidant and/or oxygen present in air and applied to hair fibers to form the dye(s).

An important group of cosmetic compositions in the hair coloring business are compositions which are present in a cream-like state at the temperature of application (this is usually between 20-35° C.). The primary intermediates employed in these cosmetic compositions are usually derivatives of benzene, e.g. p-phenylenediamines, o- and p-amino phenols or heterocyclic compounds such as 4,5-diamino pyrazoles or tetraamino pyrimidine. Primary intermediates which are combined with color coupling agents open the way for realizing a broad color spectrum. Preferred color coupling agents are resorcinol and derivatives thereof, m-aminophenols, m-phenylenediamines, 1-naphthol, and di-, tri- and tetra-substituted pyridines.

In addition to the aforementioned components, cosmetic ready-to-use compositions based on oxidative dyes contain at least one oxidant. This component is usually referred to as "the activator". The most common activator used today is hydrogen peroxide.

Cosmetic compositions based on oxidative dyes are usually manufactured and provided as two component kits, wherein one kit component has a basic pH and comprises the primary intermediates and the color coupling agents. The second kit component comprises a hydrogen peroxide composition which is usually stabilized by an amount of acid. Usually, both kit components are preferentially provided in cream- or gel-like form. Prior to use, a ready-to-use composition is produced by mixing both kit components either by stirring in a bowl or by shaking in a container, e.g. a bottle or a jar. The ready-to-use mixture is then applied to the hair using a brush or an applicator tool. Preferably, coloring mixtures have a certain, higher viscosity in order to prevent dripping during the treatment of the hair. Optimum results in the oxidative coloring of hair are achieved by ready-to-use mixtures which are adjusted to a pH in the range of from 9.0 to 10.5. Usually, the kit components are mixed directly prior to application to the hair in a ratio of from 1:1 to 1:3. Ideally, mixing is performed immediately prior to application to the hair so that formation of the oxidative dyes (the color) does not occur before the mixture is applied to the hair.

A common configuration of cosmetic compositions in cream-like form comprises at least long-chain fatty alcohols, water and one or more emulsifiers. The choice of the emulsifier system strongly determines the properties of the creams.

A first common type of emulsifier is an anionic emulsifier, wherein sodium laureth sulphate is most widely employed. However, creams using anionic emulsifiers often exhibit poor compatibility with cationic hair care products. As a consequence, combing of hair is tedious during hair treatment with this particular cosmetic composition, thus making the even root-to-tip distribution of the cream on the hair difficult. Furthermore, these difficulties in combing hair remain after washing of the hair, i.e. after the removal of the cosmetic composition. The standard way to address this problem is to apply a hair care product after washing of the hair. However, model customers (also called "models") associate damage of the hair with the haptic of the hair directly after the washing step. Moreover, the hair care products cannot be formulated into the ready-to-use mixture, since hair care products usually comprise compounds with cationic groups which in the current case would form ion pairs with the named anionic emulsifier present in the cosmetic composition. Accordingly, the effect of hair care products would be eliminated when the hair care product comes into contact with the cosmetic composition.

Compositions with non-ionic emulsifiers have been developed to overcome the drawbacks and difficulties arising from the use of anionic emulsifiers. Using combinations of waxes and non-ionic emulsifiers allows for formulating hair care products into the ready-to-use mixtures. However, the amount of dyes which can be formulated into the cosmetic composition is limited, since numerous dyes are present as adducts with an acid and salts do not dissolve well in such neutral environments. With regard to cosmetic compositions based on non-ionic systems, a common developing agent is para-phenylenediamine, which is usually employed as a free base. However, modern colorants use derivatives of p-phenylenediamine due to the evaluation by the Scientific Committee on consumer Safety (SCCS). Unfortunately, the only commercial derivates of p-phenylenediamine are sulphuric acid adducts, e.g. Toluene-2,5-diamine sulphate or Hydroxyethyl-p-phenylenediamine sulfate (both INCI names). When sulphuric acid adducts are used to form a cosmetic nonionic cream, the cream becomes more and more unstable with increasing amounts of dyes, results of this can include up to totally unsuccessful formulation attempts ab initio.

A third group of emulsifiers which are used for manufacturing colorants are cationic emulsifiers. Creams comprising cationic emulsifiers are sufficiently stable with regard to technical requirements, i.e. manufacture and storage. However, cationic emulsifiers are potentially irritating to skin. Moreover, over-caring of the hair may occur since cationic emulsifiers expose a strong affinity to the hair which may result in unfavorably heavy and greasy looking hair.

Numerous colorants which comprise common ingredients such as glycol mono or distearates have a tendency to cause thickening of the cosmetic composition over time, e.g. when in stock for several months. Thickening complicates dosage and makes thorough mixing more demanding and time consuming. This is perceived by the hairdresser as a disadvantage. Moreover, such creams tend to be sticky and doughy and can cause strings to form from the bowl to the hair upon application.

A recent trend in the manufacture of cosmetic compositions for hair coloring treatments is to avoid ammonia because of its odor. A substitute for this has been monoethanolamine. However, substitution cannot be performed in equimolar amounts because of the skin irritating potential of monoethanolamine. Furthermore, if the amount of monoethanolamine is reduced to dermatologically acceptable amounts, lightening of the melanin of hair is insufficient. Accordingly, monoethanolamine and hydrogen peroxide are usually combined in such cosmetic compositions. Since lightening with monoethanolamine and hydrogen peroxide is less strong compared to ammonia, cosmetic creams for coloring hair based on monoethanolamine and hydrogen peroxide are classified as demi-permanent. The main application of these products is to camouflage grey hair or for hair which is colored in shades darker than the natural shade.

DE19527121 A1 describes a combination of amino acids, oligo peptides and some alkanolamines, in particular monoethanolamine and basic amino acids. Monoethanolamine is preferred. However, it is mentioned in DE19527121A1 that creams with more than 6 wt. % of amino acid tend to be unstable.

WO 2004/108102 A1 describes a system, in which carbonate salts and hydrogen peroxide are mixed forming peroxy monocarbonate ions in situ which then lighten the pigments of the hair. In order to avoid unwanted secondary effects, a radical scavenger is added, preferably alkanolamines or amino acids. Tests with these systems showed that lightening occurs to all three; a. to natural pigments of hair, b. to colored hair to which a coloring cosmetic composition was applied in previous treatments, and c. to the dyes formed in the ready-to-use mixture of the current treatment. Optimum results using this system are obtained after around 10 minutes and decline steadily afterwards. Since lightening of natural pigments is a rather time consuming process compared to the color formation, competing discoloration of colored hair may occur, such systems are therefore not suited for professional hair coloring treatment.

Another cosmetic coloring system based on mineral oil and monoethanolamine as alkaline agent was introduced into the market some time ago. However, excess colorant is difficult to remove from the colored hair after processing because of the high amount of mineral oil. Accordingly, special shampoos are needed. If any cosmetic coloring composition remains in the hair, breakage of the hair is then a risk. In conclusion, these systems are not suited for professional hair coloring treatment.

Another aspect in hair coloring treatments is the use of ethanolamine. Ethanol amine may react with the proteins of hair. Based on experimental results, some experts suggest to return to ammonia-based cosmetic coloring compositions and to work on measures to reduce the evaporation of ammonia (A. D. Bailey, G. Zhang and B. P. Murphy: "Comparison of damage to human hair fibers caused by monoethanolamine- and ammonia-based hair colorants"; J. Cosmet. Sci., 65, 1-9 (2014)). However, no sustainable solutions have yet been suggested to address this task. Further, the combination of ethanolamine and hydrogen peroxide causes stress to the keratinocytes. This can cause loss of hair (J.-A. Seo e.a.: "Hydrogen peroxide and monoethanolamine are the key causative ingredients for hair dye-induced dermatitis and hair loss", Journal of Dermatological Science, 66, 12-19 (2012)).

Summarizing the above, there is both an ongoing need and search, for further developing cosmetic hair coloring systems which contain an acceptable amount, as well as an acceptable type of alkaline agent, with also the means to achieve a stable cream, into which the alkaline agent and the dyes can be formulated without degrading the composition.

Despite all efforts of the past to provide cosmetic hair coloring compositions which satisfy the customers' as well as the hairdressers' needs, there is an ongoing need for further development in this area to satisfy the markets' needs.

Accordingly, it is an object of the invention to provide a cosmetic composition which overcomes at least one, preferably two or more of the disadvantages which were described with regard to art.

Another object of the invention is to provide a cosmetic composition for the treatment of hair, in particular coloring, which is well accepted by model home users and clients of hair dressers.

Another object of the invention is to provide a cosmetic composition which is not irritating to skin, eyes or mucous membranes of model home users and clients of hair dressers.

Another object of the invention is to provide a cosmetic composition which is stable when in stock for an extended period of time.

Another object of the invention is to provide a cosmetic composition which can be applied to, worked on and rinsed off the keratin fibers, e.g. hair, with ease.

Another object of the invention is to provide a cosmetic composition which can be easily applied to hair at the hair line, which is most recently grown and has not been colored during a previous hair coloring treatment, wherein the cosmetic composition on the hair emulsifies readily when being contacted with sprayed water.

Another object of the invention is to provide a cosmetic composition which does not cause significant damage to keratin fibers.

Another object of the invention is to provide a cosmetic composition which can be used for permanent lightening and coloring of keratin fibers.

Another object of the present invention is to provide a process for the manufacture of cosmetic coloring compositions of the current composition.

Another object of the present invention is to provide an improved process for coloring keratin fibers, e.g. hair in which no after treatment products comprising care ingredients need to be applied.

A contribution to the solution of at least one of the above objects is provided by the subject-matter of the category-forming claims. The dependent sub-claims of the category-forming claims represent preferred embodiments of the invention, the subject-matter of which also makes a contribution to solving at least one of the objects mentioned above.

A first aspect of the invention is a cosmetic composition, comprising at least these components:
a. tris(hydroxymethyl)aminomethane;
b. at least one amino acid;
c. at least one organic phosphate ester compound selected from
c1. monoester of phosphates of alkoxylated fatty alcohols,
wherein the alkoxylated fatty alcohols are composed of C12-C22 fatty alcohols alkoxylated with from 1 to 50 moles of an alkylene oxide, the number of moles of alkylene oxide with respect to the moles of fatty alcohol; and
c2. diester of phosphates of non-alkoxylated fatty alcohols,
wherein the non-alkoxylated fatty alcohols are composed of C12-C22 fatty alcohols;
c3. mixtures of c1 and c2;
d. water;
with the proviso that the composition does not comprise ammonia, salts of ammonia or a source of peroxy monocarbonate ions.

The inventors incidentally found that the cosmetic composition according to the invention is surprisingly stable for the intended purpose and accepts large amounts of salts. Furthermore, the cosmetic composition according to the invention is neither stringy, nor doughy, nor sticky. Accordingly, mixtures of the current cosmetic composition and hydrogen peroxide compositions can be prepared with ease. After hair treatment, excess cosmetic compositions can be washed out with ease as well. There is no need for using any particular shampoo. It is even possible to combine the cosmetic composition according to the invention with cationic hair care products. Thus, there is no need for after treatments of the dyed hair at all to maintain the status and the haptic of healthy hair. Moreover, the composition according to the invention even allows for lightening of the hair to an extent which is usually only achieved when using permanent, ammonia based hair colorants.

A cosmetic composition in the context of the present invention refers to a composition which can be used for treatment of keratin fibers, such as hair. It can be used for lightening and/or coloring of keratin fibers. The cosmetic composition of the present invention is a cream, a gel, a dispersion or a paste, and the like. Preferably, the cosmetic composition is a cream.

A first component of the cosmetic composition of the invention is tris(hydroxymethyl)aminomethane, a compound registered under CAS-no. [77-86-1] in unprotonated form and under CAS-no. [1185-53-1] as a hydrochloride. Preferably, this compound is used in its unprotonated form.

In a preferred embodiment, the cosmetic composition comprises from 1 to 10 wt. % of tris(hydroxymethyl) aminomethane, based on the total weight of the composition.

The second component of the cosmetic composition of the invention is at least one amino acid. In general, all amino acids can be employed which are known in the art. In the present invention, the term amino acid comprises free amino acids, salts of amino acid, e.g. sodium or potassium salt with regard to the cation, as well as halides on behalf of the anion, if applicable. Preferred amino acids are selected from the group consisting of glycine, serine, asparagine, threonine, glutamine, arginine and lysine as well as α- and β-alanine, and mixtures of two or more compounds thereof. Smaller amino acids are more preferred than larger ones; wherein small and large refer to the molecular weight of the amino acid.

In a preferred embodiment of the invention, the cosmetic composition comprises a total of from 1.0 to 30 wt. %, preferably from 1.0 to 20 wt. %, or from 3.0 to 15 wt. %, or from 0.5 to 10 wt. %, or from 6 to 12 wt. % of one or more amino acids, each wt. % based on the total weight of the cosmetic composition.

The third type of component is one or a mixture of two or more organic phosphate ester compounds selected from the group consisting of
c1. monoester of phosphates of alkoxylated fatty alcohols,
c2. diester of phosphates of non-alkoxylated fatty alcohols, and
c3. mixtures of c1. and c2.

In a preferred embodiment of the invention, the cosmetic composition comprises from 0.1 to 6 wt. %, or from 0.5 to 4 wt. %, or from 1 to 2.5 wt. % in total of the one or more organic phosphate ester compounds, each wt. % based on the total weight of the cosmetic composition.

Turning to the chemical identity of the organic phosphate ester compound, numerous organic phosphate ester compounds with the aforementioned features are known in the art and appear useful in the present invention.

The monoester of phosphates of alkoxylated fatty alcohols of the composition according to the invention are composed of C12-C22 fatty alcohols alkoxylated with from 1 to 50 moles of an alkylene oxide, the number of moles of alkylene oxide with respect to the moles of fatty alcohol. Formula (1) is a general representation of an organic phosphate ester.

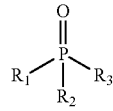

A monoester of phosphate of one or more alkoxylated fatty alcohols according to the invention is characterized as follows:
$R_x$ with x=1, 2, 3 can be same or different and $R_x$ is selected from:
aa) —OM, wherein M equals H, Na or K;
bb) —$OR_4$, wherein $R_4$ can be linear or branched and is a $C_1$-$C_{40}$ alkyl group, preferably $C_{12}$-$C_{22}$, or a $C_2$-$C_{40}$ alkenyl group, preferably $C_{12}$-$C_{20}$;
cc) —$(OCH_2CH_2)_nOCH_2CH(CH_3))_mOR_4$, wherein $R_4$ has the same meaning as identified above, n is an integer in the range of from 1 to 50;
with the proviso that at least one group $R_x$ is chosen according to aa) and at least another group is chosen according to bb) or cc).

In a further preferred embodiment, the monoester of phosphate is linear, more preferably it is defined by at least one alkyl group $R_4$, wherein $R_4$ is selected from the group consisting of $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $R_4$ being preferably one of $C_{16}$, $C_{18}$, $C_{20}$, $C_{22}$.

In a further preferred embodiment, the monoester of phosphate is linear, more preferably it is defined by at least one alkenyl group $R_4$, wherein $R_4$ is selected from the group consisting of $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $R_4$ being preferably one of $C_{16}$, $C_{18}$, $C_{20}$, $C_{22}$.

The diester of phosphates of non-alkoxylated fatty alcohols of the composition according to the invention are composed of C12-C22 non-alkoxylated fatty alcohols. With respect to formula (1), diester of phosphates of non-alkoxylated fatty alcohols according to the invention are characterized as follows:

$R_x$ with x=1, 2, 3 can be same or different, and $R_x$ is selected from:

aa) —OM, wherein M equals H, Na or K;

bb) —$OR_4$, wherein $R_4$ can be linear or branched and is a $C_1$-$C_{40}$ alkyl group, preferable $C_{12}$-$C_{22}$, or a $C_2$-$C_{40}$ alkenyl group, preferable $C_{12}$-$C_{20}$;

with the proviso that one group $R_x$ is chosen according to aa) and two groups are chosen according to bb).

In a further preferred embodiment, the monoester of phosphate is linear, more preferably it is defined by at least one alkyl group $R_4$, wherein $R_4$ is selected from the group consisting of $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $R_4$ being preferably one of $C_{16}$, $C_{18}$, $C_{20}$, $C_{22}$.

In a further preferred embodiment, the monoester of phosphate is linear, more preferably it is defined by at least one alkenyl group $R_4$, wherein $R_4$ is selected from the group consisting of $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $R_4$ being preferably one of $C_{16}$, $C_{18}$, $C_{20}$, $C_{22}$.

Moreover, mixtures of the abovementioned phosphate esters can be employed. These mixtures can comprise two or more monoester of phosphates of alkoxylated fatty alcohols and one diester of phosphate of non-alkoxylated fatty alcohols, one monoester of phosphates of alkoxylated fatty alcohols and two or more diesters of phosphate of non-alkoxylated fatty alcohols, or a mixture of two or more monoesters of phosphates of alkoxylated fatty alcohols and two or more diesters of phosphate of non-alkoxylated fatty alcohols.

In a further preferred embodiment of the invention, the at least one organic phosphate ester compound is selected from the group consisting of dicetyl phosphate, ceteth-10 phosphate, oleth-5 phosphate and dioleyl phosphate. Yet more preferred is a combination of two or more of these phosphate esters, or even all of them. All names are provided according to INCI nomenclature.

Some preferred combinations of the above phosphate esters are commercially available from Croda GmbH (41334 Nettetal, Germany) under the trade name CRODAFOS. These are, e.g.

Ceteth-10 phosphate und Dicetyl phosphate, as in CRODAFOS CES,

Ceteth-20 phosphate und dicetyl phosphate, as in CRODAFOS CS-20 ACID, and

Oleth-5 phosphate und Dioleyl phosphate, as in CRODAFOS HCE.

The above choice is in no way limiting and only serves as an example of useful commercial products in general.

The above mentioned exemplary cosmetic compositions as well as all further cosmetic compositions within the above framed scope can be used. In particular compositions manufactured therewith can comprise fatty alcohols and/or alkoxylated fatty alcohols, each with from 8 to 30 carbon atoms. Examples of these further fatty alcohols and/or alkoxylated fatty alcohols are Cetyl alcohol, Stearyl alcohol and mixtures thereof, Octyldodecanol, 2-Butyloctanol, 2-Hexyldecanol, 2-Undecylpentadecanol, Oleyl alcohol and Linoleyl alcohol (all according to INCI nomenclature).

The fourth component of the cosmetic composition according to the invention is water, preferably, demineralized water.

In a further preferred embodiment of the invention, no ammonia ($NH_3$) or ammonium salts ($NH_4X$, wherein X is an anion) are present in the cosmetic composition.

In a further preferred embodiment of the invention, no source of peroxy monocarbonate ions is present in the cosmetic composition. Examples of a source of peroxy monocarbonate ions are combinations of hydrogen peroxide with at least one carbonate ion source, which is selected from carbonate, carbamate, hydrogencarbonate, or mixtures of two or more thereof.

In a further preferred embodiment, the cosmetic composition of the invention further comprises at least one dye, which is selected from (a) at least one primary intermediate, and optionally further at least one color coupling agent;

(b) at least one direct dye; and (c) mixtures of (a) and (b).

A number of dyes can be used in the cosmetic composition of the invention. Preferred dyes are oxidative dyes selected from primary intermediates. Direct dyes are another preferred group of dyes useful in the cosmetic composition. Direct dyes are considered particularly useful for generating particular shades or reflexes. The direct dyes of the embodiment are preferably selected from the group consisting of nitro dyes, azo dyes, anthraquinone dyes and triphenylmethane dyes, each of which can be neutral, cationic, anionic or zwitterionic (also referred to as: "bipolar ion").

Regarding alternative (a), numerous primary intermediates are known to and considered suitable by those skilled in the art. In a preferred embodiment, the composition of the invention comprises a total amount of dyes in the range of from 0.01 to 12 wt. %, preferably in the range of from 0.1 to 10 wt. %, yet more preferably in the range of from 0.1 to 8 wt. %, in total of one or more dyes, each based on the total weight of the composition.

Preferred primary intermediates are selected from the group consisting of p-Phenylenediamines, p-Aminophenols, o-Aminophenols, 4,5-Diaminopyrazoles, Pyrimidines. Yet more preferred are 1,4-diamino-benzene; 1,4-diamino-2-methyl-benzene; 1,4-diamino-2-(2-hydroxyethyl)-benzene; 1,4-diamino-2,3-dimethyl-benzene; 1,4-diamino-2,6-dimethyl-benzene; 1,4-diamino-2-methoxymethyl-benzene; 1,4-diamino-2-chloro-benzene; 4-[di(2-hydroxyethyl)amino]-aniline; 2,2'-({2-[(4-aminophenyl)amino]ethyl}imino)diethanol; (4-aminophenyl)-(3-(imidazol-1-yl)propyl)amine; N,N'-bis((3-hydroxyethyl)-N,N'-bis(4'-aminophenyl)-1,3-diaminopropanol; 4-aminophenol; 4-amino-3-methylphenol; bis(5-amino-2-hydroxyphenyl)methane; 2-amino-5-ethylphenol; 4,5-diamino-1-(2-hydroxyethyl)-1H-pyrazole; 2,3-diaminodihydroxypyrazolo pyrazolone dimethosulfonate; 2,4,5,6-tetraaminopyrimidine; and a combination of two or more thereof. The primary intermediates can also be present in adduct form with an acid, e.g. hydrochloric acid or sulfuric acid. 1,4-diamino-2-methoxymethyl-benzene is a particularly preferred choice of one primary intermediate.

Though not absolutely necessary, at least one color coupling agent is often added to the at least one primary amine. It is a further embodiment of the present invention for alternative (a) to combine at least one primary intermediate with at least one color coupling agent. Preferred color coupling agents are selected from the group consisting of 1,3-dihydroxybenzene; 4-chloro-1,3-dihydroxybenzene; 1,3-dihydroxy-2-methylbenzene; 3-aminophenol; 5-amino-2-methylphenol; 5-amino-4-chloro-2-methylphenol; 3-amino-2,6-dimethylphenol; 2-methyl-5-hydroxyethylaminophenol; 3-amino-2,4-dichlorophenol; 3,4-dihydro-2H-1, 4-benzoxazin-6-ol; N-hydroxyethyl-3,4-methylenedioxyaniline; 3,4-dihydro-6-hydroxy-2H-1,4-benzoxazine; 6-amino-3,4-dihydro-2H-1,4-benzoxazine; 2,4-diamino-1-(2-hydroxyethoxy)benzene; 2-amino-4-[(2-hydroxyethyl)amino]anisole; 1,3-bis(2,4-diaminophenoxy)propane; 1-methyl-2,6-bis-(2-hydroxyethylamino)-benzene; 1-naphthol; 2-methyl-1-naphthol; 1,5-naphthalenediol; 2,7-naphthalenediol; 2,6-diaminopyridine; 2,6-dihydroxy-3,4-dimethylpyridine; 3,5-diamino-2,6-dimethoxypyridine; 2-amino-3-hydroxypyridine; 6-methoxy-2-methylamino-3-aminopyridine; 3-methyl-1-phenyl-5-pyrazolone; 6-hydroxyindole; 5,6-dihydroxyindole; and a combination of two or more thereof.

Color coupling agents which have one or two amino groups can be present as free amines, or partially or totally in adduct form with an acid, e.g. as adduct with hydrochloric acid or sulfuric acid.

Preferred nitro dyes are selected from the group consisting of 2-Amino-3-nitrophenol; 2-[(2-Hydroxyethyl)amino]-1-methoxy-5-nitrobenzene; 1-(2-Hydroxyethoxy)-3-methylamino-4-nitrobenzene; 2,3-(Dihydroxypropoxy)-3-methylamino-4-nitrobenzene; 1-[(2-Ureidoethyl)amino]-4-nitrobenzene; 4-[(2-Hydroxyethyl)amino]-3-nitro-1-methylbenzene; 1-[(2-Hydroxyethyl)amino]-2-nitrobenzene (HC Yellow No. 2); 1-(2-Hydroxyethoxy)-2-[(2-hydroxyethyl)amino]-5-nitrobenzene (HC Yellow No. 4); 1-Amino-2-[(2-hydroxyethyl)amino]-5-nitrobenzene (HC Yellow No. 5); 4-[(2,3-Dihydroxypropyl)amino]-3-nitro-1-trifluoromethylbenzene (HC Yellow No. 6); 3-[(2-Aminoethyl)amino]-1-methoxy-4-nitrobenzene hydrochloride (HC Yellow No. 9); 1-Chloro-2,4-bis-[(2-hydroxyethyl)amino]-5-nitrobenzene (HC Yellow No. 10); 2-[(2-Hydroxyethyl)amino]-5-nitrophenol (HC Yellow No. 11); 1-Chloro-4-[(2-hydroxyethyl)amino]-3-nitrobenzene (HC Yellow No. 12); 4-[(2-Hydroxyethyl)amino]-3-nitro-1-trifluoromethyl-benzene (HC Yellow No. 13); 4-[(2-Hydroxyethyl)amino]-3-nitrobenzonitrile (HC Yellow No. 14); 4-[(2-Hydroxyethyl)amino]-3-nitro-benzamide (HC Yellow No. 15); 1,4-diamino-2-nitrobenzene; 1,4-Bis[(2-hydroxyethyl)amino]-2-nitrobenzene; 2-Amino-4,6-dinitro-phenol; 4-Amino-3-nitrophenol; 1-Amino-5-chloro-4-[(2-hydroxyethyl)amino]-2-nitrobenzene; 4-[(2-Hydroxyethyl)amino]-3-nitrophenol; 1-[(2-Aminoethyl)amino]-4-(2-hydroxyethoxy)-2-nitrobenzene (HC Orange No. 2); 4-(2,3-Dihydroxypropoxy)-1-[(2-hydroxyethyl)amino]-2-nitrobenzene (HC Orange No. 3); 2-[(2-Hydroxyethyl)amino]-4,6-dinitro-phenol; 4-Ethyl-amino-3-nitrobenzoic acid; 2-[(4-Amino-2-nitrophenyl)amino]-benzoic acid; 2-Chloro-6-ethylamino-4-nitrophenol; 2-Amino-6-chloro-4-nitrophenol; 4-[(3-Hydroxypropyl)amino]-3-nitrophenol; 2,5-Diamino-6-nitropyridine; 1,2,3,4-Tetrahydro-6-nitroquinoxaline; 4-Amino-2-nitro-diphenylamine (HC Red No. 1); 4-Amino-1-[(2-hydroxyethyl)amino]-2-nitrobenzene (HC Red No. 3); 1-Amino-4-[(2-hydroxyethyl)amino]-2-nitrobenzene (HC Red No. 7); 1-Amino-5-chloro-4-[(2,3-dihydroxypropyl)amino]-2-nitrobenzene (HC Red No. 10); 5-Chloro-1,4-[ di(2,3-dihydroxypropyl)amino]-2-nitrobenzene (HC Red No. 11); 1-Amino-4-[di(2-hydroxyethyl)amino]-2-nitrobenzene hydrochloride (HC Red No. 13); 7-Amino-3,4-dihydro-6-nitro-2H-1,4-benzoxazine (HC Red No. 14); 1-Amino-3-methyl-4-[(2-hydroxyethyl)amino]-6-nitrobenzene (HC Violet No. 1); 1-(3-Hydroxypropylamino)-4-[di(2-hydroxyethyl)amino]-2-nitrobenzene (HC Violet No. 2); 1-(2-Hydroxyethyl)amino-2-nitro-4-[ di(2-hydroxyethyl)amino]-benzene (HC Blue No. 2); 1-Methylamino-4-[methyl-(2,3-dihydroxypropyl)amino]-2-nitrobenzene (HC Blue No. 6); 1-[(2,3-Dihydroxypropyl)amino]-4-[ethyl-(2-hydroxyethyl)amino]-2-nitrobenzene hydrochloride (HC Blue No. 9); 1-[(2,3-Dihydroxypropyl)amino]-4-[methyl-(2-hydroxyethyl)amino]-2-nitrobenzene (HC Blue No. 10); 4-[Di(2-hydroxyethyl)amino]-1-[(2-methoxyethyl)amino]-2-nitrobenzene (HC Blue No. 11); 4-[Ethyl-(2-hydroxyethyl)amino]-1-[(2-hydroxyethyl)amino]-2-nitrobenzene hydrochloride (HC Blue No. 12); 2-((4-Amino-2-nitrophenyl)amino)-5-dimethylaminobenzoic acid (HC Blue No. 13), and combinations of two or more thereof.

Preferred cationic dyes are selected from the group consisting of Basic Yellow 57, Basic Brown 16, Basic Brown 17, Basic Red 76, Basic Red 118, Basic Blue 99, Basic Yellow 87, Basic Orange 31, Basic Red 51, Basic Violet 2, Basic Blue 75, Basic Blue 77, Basic Blue 124, HC Blue 15, HC Blue 16, HC Blue 17, and combinations of two or more thereof.

Two or more of the above mentioned dyes and/or color coupling agent-primary intermediate combinations, or combinations of one or more dyes with one or more combinations of color coupling agent and primary intermediate can be used according to a further preferred embodiment.

A further preferred embodiment of the cosmetic composition of the invention further comprises at least one non-ionic surfactant, which can be present in an amount of from 1.0 to 8.0 wt. %, or from 1.0 to 4.0 wt. %, or from 1.0 to 2.0 wt. %, each wt. % based on the total weight of the cosmetic composition.

Preferred non-ionic surfactants can be based on
aa. fatty alcohols or fatty acids, each of which consist preferably of a carbon chain of from 12 to 22 carbon atoms and an alkoxy fragment obtained from addition of ethylene oxide or propylene oxide, or a mixture of both to the fatty alcohol or fatty acid species. More preferably, the number of alkoxy repeat units is in the range of from 2 to 100 in the case of ethylene oxide and 0 to 5 in the case of propylene oxide, and block or statistical combinations of both of them, each with respect to one fatty alcohol or fatty acid molecule.
bb. alkyl phenols wherein the alkyl fragment is a linear or branched alkyl chain of 8 to 15 carbon atoms.
cc. Mono- or diesters of fatty acids with a linear carbon chain of from 12 to 22 carbon atoms and ethoxylated glycerols, wherein the glycerol is reacted with 5 to 60 mol ethylene oxide, the number of mols per hydroxyl group of glycerol.
dd. alkylmonoglycosides and alkyloligoglycosides, wherein the alkyl fragment has 8 to 22 carbon atoms, as well as ethoxylated derivatives thereof, wherein the number of ethoxy groups is in the range of from 5 to 60 repeat units per alkyl fragment;
ee. ethoxylated castor oil with a ratio of ethyoxy groups to the castor oil fatty acids is in the range of from 5:1 to 50:1; ethoxylated hardened castor oil.
ff. ethyoxylated sorbitan fatty acid ester comprising of from 2 to 160 ethyleneoxy units; and
gg. ethoxylated fatty acid alkanol amides.

In a further preferred embodiment of the cosmetic composition, two or more of the above identified non-ionic surfactants can be present.

The composition of the invention can comprise further components. Amongst these, direct polymers, natural or vegetable oils, organic solvents, complex forming agents, acids and bases to regulate pH and antioxidants are most common.

In a further embodiment of the invention, the cosmetic composition comprises one or more oils of natural or synthetic origin. The term "oil" refers in the context of the present invention to an organic compound that is insoluble in water at room temperature (25° C.) and at atmospheric pressure (1013 hPa). Insoluble in the present context means that the compound referred to has a solubility of less than 5%, preferably than 1%, yet more preferred less than 0.1%, in a mentioned fluid, with respect to the total amount of reference fluid. Usually, oils can be dissolved in many organic solvents under the same temperature and pressure conditions. Examples of common organic solvents are chloroform, ethanol and benzene.

Preferred oils are fatty acid esters, fatty alcohol esters, mineral oil or lower alkanes, e.g. linear or branched alkanes. Further preferred are silicon oils, e.g. alkoxylated silicone oils, or silicone oils, which comprise terminal amino groups, and/or tertiary amino groups in the side chain.

In a further preferred embodiment of the invention, the cosmetic composition contains less than 20 wt. %, or less than 12 wt. %, or less than 8 wt. % of mineral oil, based on the total weight of the composition. Yet more preferred, the cosmetic composition of the invention contains no mineral oil, i.e. 0 wt. %, based on the total weight of the composition.

According to a further preferred embodiment of the invention, the cosmetic composition contains less than 20 wt. %, or less than 12 wt. %, or less than 8 wt. % of one or more natural oils, based on the total weight of the composition. Yet more preferred the cosmetic composition of the invention contains no natural oils, i.e. 0 wt. %, based on the total weight of the composition. Examples of natural oils are olive oil, castor oil, squalene. These oils are not ethoxylated.

According to a further preferred embodiment of the invention, the cosmetic composition can comprise polymers with cationic groups which are named Polyquaternium according to INCI. Some preferred examples of Polyquatrenium compounds are Polyquaternium-37 (Poly(2-methacryloxyethyltrimethylammonium chloride)), Polyquaternium-4 (Hydroxyethyl cellulose dimethyl diallylammonium chloride copolymer), Polyquaternium-10 (Quaternized hydroxyethyl cellulose), Polyquaternium-7 (Copolymer of acrylamide and diallyldimethylammonium chloride). Particularly preferred cationic polymers are Polyquaternium-22 (Copolymer of acrylic acid and diallyldimethylammonium Chloride) and Polyquaternium-39 (Terpolymer of acrylic acid, acrylamide and diallyldimethylammonium Chloride), both comprising diallyldimethylammonium chloride (DADMAC).

Another preferred group of cationic polymer is copolymers of vinylpyrrolidone and N-vinylimidazolium salts (Tradename: "Luviquat®"). The cosmetic composition of the invention can comprise a combination of two or more of the above mentioned cationic polymers.

In a further preferred embodiment of the invention, the cosmetic composition comprises an amount of one or more organic alcohols in the range of from 0.1 to 6.0 wt. %, or from 1.0 to 3.0 wt. %, each wt. % based on the total weight of the composition. Preferably, the cosmetic composition of the invention comprises at least one organic alcohol selected from the group consisting of ethanol, isopropanol, ethylene glycol, propylene glycol, butylene glycol and hexylene glycol, polyglycoles like diethylene glycol, dipropylene glycol as well as polyethyleneglycols and polypropyleneglycols; Triols like glycerol and trimethylol propane, as well as combinations of two or more thereof.

In a further preferred embodiment of the invention, the cosmetic composition comprises an amount of one or more organic ethers in the range of from 0.1 to 6.0 wt. %, or from 1.0 to 3.0 wt. %, each wt. % based on the total weight of the composition. Preferably, the cosmetic composition of the invention comprises at least one organic ether selected from ethoxydiglycol, 1-butoxypropan-2-ol and dimethyl isosorbide.

In a further preferred embodiment of the invention, the cosmetic composition contains complex forming agents. The complex forming agents can be present in the cosmetic composition of the invention in an amount of from 0.01 to 0.5 wt. %, based on the total weight of the composition. The complex forming agents are added to bind iron, copper or other metal ions.

Numerous complex forming agents are known in the art and appear useful in the present invention. Preferred examples are salicylic acid, 8-hydroxyquinoline, 1-hydroxyethane-1,1-diphosphonic acid, amino-tri-(methylene phosphonic acid), ethylenediaminetetraacetic acid (EDTA), ethylenediaminedisuccinic acid (EDDS), and the sodium salts thereof, or a combination of two or more thereof. In the case of EDDS, the amount of complex forming agent can be in the range of from 0.01 to 2.5 wt. %, based on the total weight of the cosmetic composition.

In a further preferred embodiment of the invention, the cosmetic composition contains viscosity regulating agents, e.g. thickeners. The composition preferably comprises from 0.01 wt. % to about 5 wt. %, based on the total amount of the composition.

Preferred examples of viscosity regulating agents are agar-agar, guar gum, alginates, xanthan gum, natural rubber, Arabic gum, karaya gum, locust bean flour, linseed gums, dextrans, cellulose derivatives like methyl cellulose, hydroxylalkyl cellulose, carboxymethyl cellulose, starch derivatives like amylose, amylopectin, dextrins, clays like bentonite and synthetic hydrocolloids like polyvinyl alcohols, or a combination of two or more thereof.

In a further preferred embodiment of the invention, some acids and bases were added to the cosmetic composition in order to adjust the pH of the composition of the invention. Accordingly, acids like hydrochloric acid, sulphuric acid, phosphoric acid, citric acid and malic acid, or combinations thereof can be present in the cosmetic composition of the invention. Preferred bases are sodium hydroxide and potassium hydroxide, or mixtures thereof. It is even possible to combine one or more acid with one or more base in the cosmetic composition which at least partially eliminates acid and base effects but might be beneficial for other purposes not described herein.

In a further preferred embodiment of the invention, the pH value of the cosmetic composition of the invention is in the range of from 6 to 12, more preferably in the range of from 9.5 to 11.5. The aforementioned acids and bases are preferably used to adjust the pH of the composition to a value within this range.

In a further preferred embodiment of the invention, the cosmetic composition contains one or more antioxidants. Preferred antioxidants are ascorbic acid and iso-ascorbic acid. These antioxidants are added to stabilize the oxidative dyes in the composition of the invention.

In a further preferred embodiment of the invention, the cosmetic composition contains one or more reducing agents. Preferred examples are sodium sulphite, sodium metabisulfite, sodium dithionite and mixtures thereof as well as mixtures of one or more antioxidant with one or more reducing agents.

A second aspect of the invention is a process of manufacturing a dispersion, wherein the dispersion comprises a cosmetic composition of the invention as described in the first aspect of the invention, wherein the process comprises at least these steps:

i. providing water, and optionally a viscosity regulating agent as mentioned above;
ii. providing the at least one organic phosphate ester compound, and optionally further fatty alcohols and non-ionic emulsifiers;
iii. mixing the compounds provided in step i. to ii., further providing and adding an inorganic base until a pH in the range of from 8 to 12, preferably of from 10 to 11, is reached;
iv. providing tris(hydroxymethyl)aminomethane;
v. applying heat to the mixture obtained from step iv. to achieve a temperature of 85° C. and maintaining this temperature for at least 10 minutes;
vi. cooling the mixture to 50° C.;
vii. adding to mixture I an aqueous mixture II which aqueous mixture II comprises at least one amino acid, optionally dyes and further components, whereby the pH of mixture II is adjusted to a pH in the range of from 8 to 12, preferably of from 10 to 11, by an amount of inorganic base;
viii. cooling the resulting mixture III obtained in step vii. to 40° C. and homogenizing, followed by cooling to room temperature;
whereby the dispersion is obtained.

The term dispersion in context of the present invention is defined as a system in which at least two distinguishable phases are present. At least one of these phases is liquid and forms a continuous phase. At least another phase is discontinuous in and of a different composition with regard to the first phase. The phases of the dispersion can be all liquids, but also at least one of the discontinuous phases can be solid. The term dispersion preferably further stands for a system which does not exhibit phase segregation or precipitation when being stocked at a temperature of 50° C. for a certain period of time. Three months are a preferred certain period of time. One way to observe phase segregation or precipitation is inspection with the eye.

The cosmetic composition of the invention can be prepared according to different procedures. According to a conventional protocol, the composition of the invention is produced in a batch process. Since the viscosity of the composition of the invention is rather low (i.e. in the range of from 1 to 40 Pa·s), the composition is well suited for being manufactured in a continuous process. Accordingly, an embodiment of the process of the invention is performed as a continuous process. In both processes, continuous or batch, a dye-free cosmetic composition is prepared in a first step. A particular advantage of this cosmetic composition of the invention is its versatility. For example, tris(hydroxymethyl)aminomethane as well as optional further bases can be added at any stage of the process and either to the cosmetic composition of the invention or to the dye, as part of the dye component. This is a preferred embodiment, in particular when performing a continuous process of manufacture, when generation of heat should be avoided which arises from acid-base neutralization. Control of heat generation is advantageous because the viscosity of mixtures in the production process often varies with temperature. Such conditions are prerequisites for using a static mixer or a dynamic mixer, if the cosmetic composition of the invention should be adopted to a specific shade employing the principle of delayed differentiation. Preferably, double-chamber pumps are employed with which the constant pressure and output can be adjusted to the viscosity of the fluid. Preferably the pressure can be selected in the range of from 1 to 200 bar. Manufacturing the dispersion of the invention using a continuous process eliminates time consuming batch production, especially the time consuming cleaning cycles. Furthermore, different shades can be produced within short delays because a static mixer has low mixing volume and in this case no extensive cleaning of mixing apparatus is necessary. This is of considerable economic advantage.

Further components of the cosmetic composition as described above with respect to the first aspect of the invention can be added. Some of them are preferably added prior to mixing and mixed in step iv. and/or in step vii. Yet more preferably, the further components are added in step vii.

A third aspect of the invention is a coloring composition for keratin fibers which comprises a dispersion comprising the cosmetic composition described in the first aspect of the invention, or a dispersion obtained by the process according to the second aspect to the invention. Further embodiments of the third aspect of the invention are similar embodiments to those discussed in the first aspect of the invention. Numerous kinds of keratin fibers are known to those skilled in the art. Preferred keratin fibers in the context of the present invention are human hair and animal hair.

A fourth aspect of the invention is a kit for coloring keratin fibers, comprising in individually packaged form at least two kit components:
I a cosmetic composition as claimed in the first aspect of the invention and embodiments thereof, or a cosmetic composition obtainable by a process according to the second aspect of the invention and embodiments thereof; and
II a developer composition comprising an oxidizing agent.

In a preferred embodiment, the oxidizing agent of the kit comprises an aqueous solution of hydrogen peroxide. In a further preferred embodiment, the amount of hydrogen peroxide in the aqueous solution is in the range of from 2 to 12 wt. %, with respect to the total weight of the aqueous solution.

Oxidative hair coloring compositions like those according to the present invention are usually sold in kits comprising, in individually packaged components such as separate containers, a first container containing the tint component comprising dyes, and an alkaline agent and; the second container containing a developer composition comprising the oxidizing agent (usually hydrogen peroxide). The consumer mixes the content of the first container and the second container together immediately before use, thereby, obtaining a ready-to-use composition and applies it onto the hair.

A fifth aspect of the invention is a ready-to-use composition obtainable by mixing the kit components described in the fourth aspect of the invention. Preferably, the kit components are mixed directly prior to application to the keratin fibers, e.g. hair. This enables best performance of the ready-to-use composition.

In a preferred embodiment, the ratio of the kit components I and II is in the range of from 1:1 and 1:3, the amounts in the ratios based on parts by weight of components I and II.

After working the ready-to-use composition for a few minutes (to insure uniform application to all of the hair), a ready-to-use composition is allowed to remain on the hair for an amount of time sufficient for obtaining the target shade. The remaining period is in the range of from 5 to 90 minutes, preferably 10 to 60 minutes, and usually about 30 minutes.

In the kit composition of the invention, a third container may be present. In this event, all three components can either be mixed immediately before use and applied together.

Preferably this procedure is carried out if, for instance, the third container comprises a dye which does not support conditions present in the tint (e.g. reducing conditions). Alternatively, the content of the third container is applied after an optional rinse step immediately after processing as a post-treatment; in such cases the container comprises a conditioner.

A sixth aspect of the invention is a process for coloring keratin fibers, comprising the steps of:
I. providing keratin fibers;
II. contacting the keratin fibers of step I. with the ready-to-use composition described in the fifth aspect of the invention and allowing the ready-to-use composition to remain on the keratin fibers for a period of time, sufficient to obtain the desired color result;
III. optionally rinsing the keratin fibers;
IV. optionally drying the keratin fibers.

Numerous kinds of keratin fibers are known to those skilled in the art. Preferred keratin fibers in the context of the present invention are human hair and animal hair. The process for coloring keratin fibers is described in the following with regard to human hair. This is not intended to limit the scope of the claimed process. To the contrary, it is understood that the process can be applied in the same way to any other kind of keratinous material.

Oxidative hair coloring compositions like those according to the present invention are usually sold in kits comprising, in individually packaged components such as separate containers, a first container containing the dye component comprising the oxidative dye, precursors and a base and; the second container containing a developer composition comprising the oxidizing agent (usually hydrogen peroxide). The consumer mixes the content of the first container and the second container together immediately before use thereby obtaining a ready-to-use composition and applies it onto the hair.

After processing the ready-to-use composition (to insure uniform application to all of the hair), the ready-to-use composition is allowed to remain on the hair for an amount of time sufficient for the dyeing to take place. The remaining period is in the range of from 5 to 90 minutes, preferably 10 to 60 minutes, and usually about 30 minutes. The consumer then rinses his/her hair thoroughly with tap water and allows it to dry. It is observed that the hair has changed from its original color to the desired color.

When present in the composition of the invention, the optional hair care agent can be provided in a third container. In the latter case, all three compositions can be mixed immediately before use and applied together, or the content of the third container can be applied (after an optional rinse step) as a post-treatment immediately after the ready-to-use composition resulting from the mixture of the other containers.

EXAMPLES

Figure 1:
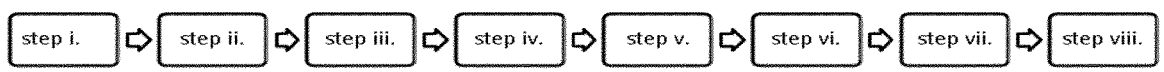
FIG. 1 shows a process of manufacturing a dispersion. The process comprises these steps: i. providing water; ii. providing of the at least one organic phosphate ester compound; iii. mixing the compounds provided in step i. to ii., further adding an inorganic base until a pH in the range of from 8 to 12, preferably of from 10 to 11, is reached; iv. providing tris(hydroxymethyl)aminomethane; v. applying heat to the mixture obtained from step iv. to achieve a temperature of 85° C. and maintaining this temperature for at least 10 minutes; vi. cooling the mixture to 50° C.; vii. adding to mixture I an aqueous mixture II which aqueous mixture II comprises at least one amino acid, optionally dyes and further components, whereby the pH of mixture II is adjusted to a pH in the range of from 8 to 12, preferably of from 10 to 11, by an amount of inorganic base; viii. cooling the resulting mixture III to 40° C. and homogenizing, followed by cooling to room temperature. At this stage, the dispersion is obtained.
Figure 2:
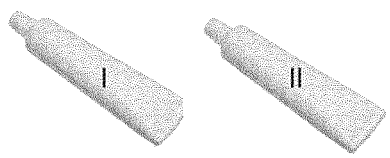
FIG. 2 shows a kit for coloring keratin fibers consisting of 2 tubes with cream.
Figure 3:
FIG. 3 shows a process for coloring keratin fibers, comprising these steps: I. providing keratin fibers; II. contacting the keratin fibers of step I. with a ready-to-use composition which was obtained by mixing the components of a kit as in FIG. 2, further allowing the ready-to-use composition to remain on the keratin fibers for a period of time; III. (optionally) rinsing the keratin fibers; IV. (optionally) drying the keratin fibers.
Figure 4:
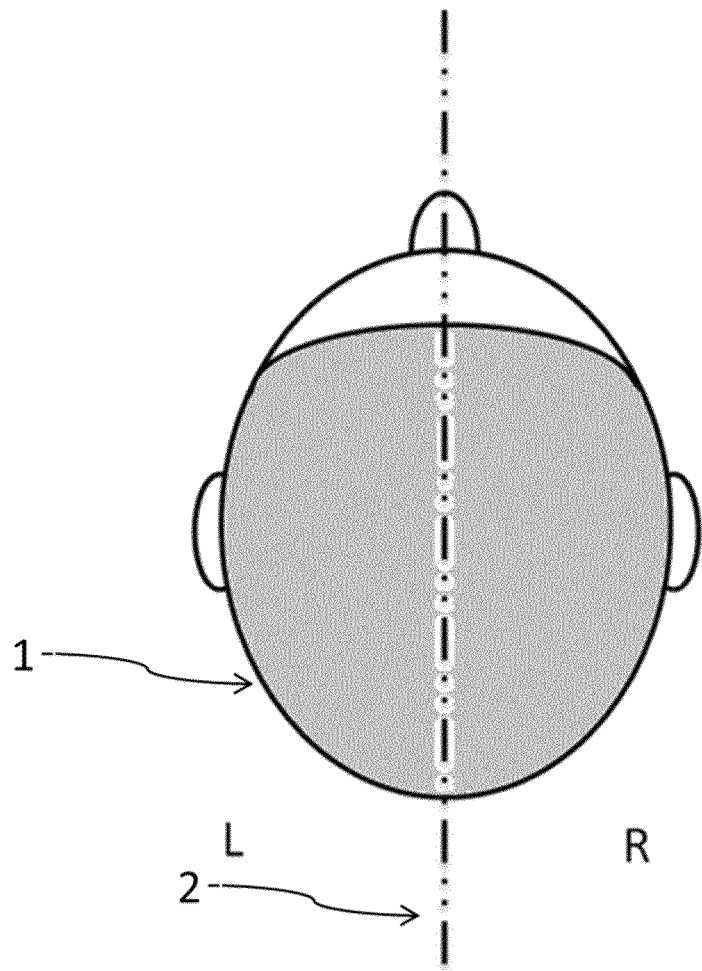
FIG. 4 is a schematic of model head 1 as discussed in Example 10. The left side L of the head with hair (not shown here) was treated with a reference coloring composition, the right side R of the head with hair (not shown here) was treated with the cosmetic coloring composition under evaluation.

The following examples illustrate some aspects of the invention. It is understood that the examples and embodiments described herein are for illustrative purposes only and that various modifications or changes in light thereof may be suggested by one skilled in the art without departing from the scope of the present invention.

Amounts mentioned in the tables below refer to wt.-% if not indicated to the contrary. When referring to rinsing or washing of hair with water in the examples, this is tap water, with a hardness of dH=8.4 (equals 1.5 mmol $CaCO_3$/liter $H_2O$). When referring to water as component of a composition (in tables, denoted as "aqua"), this is demineralized water as used for cosmetic purposes.

Comparative Examples 1-3

Comparative examples 1, 2 and 3 have been prepared based on a standard formulation. These examples are not reflective of the invention.

TABLE 1 developer compositions with hydrogen peroxide as oxidation agent

| | Developer composition | | |
|---|---|---|---|
| | 1 | 2 | 3 |
| Cetearyl alcohol | 2.0 | 2.0 | 2.0 |
| Ceteareth-50 | 0.5 | 0.5 | 0.5 |
| Phosphoric acid 85% | 0.1 | 0.1 | 0.1 |
| Hydrogen peroxide 35% | 17.1 | 25.8 | 34.3 |
| Aqua ad | 100.0 | 100.0 | 100.0 |
| Hydrogen peroxide in the developer composition | 6% | 9% | 12% |
| pH of the developer composition | 3.0 | 3.0 | 3.0 |

TABLE 2

Tint composition

| | Tint composition | | |
|---|---|---|---|
| | 1 | 2 | 3 |
| Crodaphos CES | 8.00 | 7.00 | 10.00 |
| Xanthan gum | 0.10 | 0.10 | 0.30 |
| Propylene glycol | 3.00 | 3.00 | 5.00 |
| Glycine | 5.00 | 8.00 | 12.00 |
| Arginine | 1.00 | — | — |
| Sodium hydroxide | 4.90 | 4.55 | 6.80 |
| Ascorbic acid | 0.30 | 0.30 | 0.30 |
| Sodium sulfite | 0.30 | 0.30 | 0.30 |
| EDTA | 0.20 | 0.20 | 0.20 |
| p-Toluenediamine sulfate | 4.00 | — | 0.04 |
| Methoxy-methyl-p-phenylenediamine | — | 0.82 | — |
| Resorcinol | 1.00 | 0.45 | 0.015 |
| m-Aminophenol | 0.70 | 0.05 | 0.002 |
| 2,4-Diaminophenoxyethanol sulfate | 0.60 | — | 0.010 |
| 2-Methylresorcinol | — | 0.10 | — |
| Tris(hydroxymethyl)aminomethane | 3.00 | 5.00 | 5.00 |
| Aqua, ad | 100 | 100 | 100 |

Tint composition 1 (according to table 2) was mixed in 1:1 ratio with developer composition 1 (according table 1) and applied onto medium-blond human hair. After remaining on the hair for 30 minutes, the hair was rinsed with water ($T_{water}$=30° C.) and dried. The color of the treated hair was black.

Tint composition 2 (according to table 2) was mixed in 1:1 ratio with developer composition 1 (according table 1) and applied onto human hair with 50% grey hair. After remaining on the hair for 30 minutes, the hair was rinsed with water ($T_{water}$=30° C.) and dried. The color of the treated hair was medium-blond.

Tint composition 3 (according to table 2) was mixed in 1:1 ratio with developer composition 3 (according table 1) and applied onto human hair of shade 7/0. After remaining on the hair for 30 minutes, the hair was rinsed with water ($T_{water}$=30° C.) and dried. The color of the treated hair was light-blond.

Examples 4-7

TABLE 3

Tint composition

| | Tint composition | | | |
|---|---|---|---|---|
| | 4 | 5 | 6 | 7 |
| Crodaphos CES | 8.00 | 7.00 | 10.00 | 10.00 |
| Cetearyl alcohol | 4.00 | 2.00 | — | 2.00 |
| Lauryl alcohol | — | 0.50 | 1.00 | — |
| Myristyl alcohol | — | — | 1.00 | 0.30 |
| Stearyl alcohol | — | — | 3.00 | — |
| Ceteareth-25 | 0.20 | — | — | — |
| Steareth-21 | — | — | 0.50 | — |
| Ceteareth-50 | — | 0.40 | — | — |
| Xanthan gum | 0.01 | — | 0.03 | — |
| Propylene glycol | 3.00 | 3.00 | 5.00 | 5.00 |
| Glycine | 6.00 | 8.00 | 12.00 | 8.00 |
| Sodium hydroxide | 3.20 | 4.30 | 6.40 | 4.30 |
| Ascorbic acid | 0.30 | 0.30 | 0.30 | 0.30 |
| Sodium sulfite | 0.30 | 0.30 | 0.30 | 0.30 |
| EDTA | 0.20 | 0.20 | 0.20 | 0.20 |
| p-Toluenediamine sulfate | 4.00 | — | 0.04 | — |
| Methoxy-methyl-p-phenylenediamine | — | 0.82 | — | 0.200 |
| 4,5-Diamino-1-hydroxyethyl pyrazole sulfate | — | — | — | 1.500 |
| Resorcinol | 1.00 | 0.45 | 0.015 | — |
| m-Aminophenol | 0.70 | 0.05 | 0.002 | — |
| 2,4-Diaminophenoxyethanol sulfate | 0.60 | — | 0.010 | — |
| 2-Methylresorcinol | — | 0.10 | — | — |
| 4-Amino-2-hydroxytoluene | — | — | — | 0.940 |
| Tris(hydroxymethyl)aminomethane | 3.00 | 5.00 | 5.00 | 5.00 |
| Polyquaternium-23 | 0.30 | — | — | — |
| Polyquaternium-7 | — | — | — | 0.50 |
| Aqua ad | 100 | 100 | 100 | 100 |

Tint composition 4 (according to table 3) was mixed in 1:1 ratio with developer composition 1 (according table 1) and applied onto human hair with 50% grey hair. After remaining on the hair for 30 minutes, the hair was rinsed with water ($T_{water}$=30° C.) and dried. The color of the treated hair was black.

Tint composition 5 (according to table 3) was mixed in 1:1 ratio with developer composition 1 (according table 1) and applied onto human hair with a grey index of 50%. After remaining on the hair for 30 minutes, the hair was rinsed with water ($T_{water}$=30° C.) and dried. The color of the treated hair was medium-blond.

Tint composition 6 (according to table 3) was mixed in 1:2 ratio with developer composition 3 (according table 1) and applied onto human hair with a grey index of 50%. After remaining on the hair for 30 minutes, the hair was rinsed with water ($T_{water}$=30° C.) and dried. The color of the treated hair was light-blond.

Tint composition 7 (according to table 3) was mixed in 1:1 ratio with developer composition 1 (according table 1) and applied onto human hair with a grey index of 50%. After remaining on the hair for 30 minutes, the hair was rinsed with water ($T_{water}$=30° C.) and dried. The color of the treated hair was red.

Example 8: Lightening of Hair

The following composition has no dye. Such composition has the effect of lightening hair once mixed with a developer composition and applied.

TABLE 4

| Lightening composition | |
|---|---|
| Tris(hydroxymethyl)aminomethane | 5.0 |
| Sodium glycinate | 18.4 |
| Sodium-β-alaninate | 2.2 |
| Crodaphos CES | 6.0 |
| Lorol spez | 4.0 |
| Lanette O | 3.0 |
| Lanette 18 | 2.0 |
| Propylene glycol 1,2 | 2.0 |
| Ceteareth-25 | 0.4 |
| Xanthan gum | 0.4 |
| Sodium sulfite | 0.4 |
| Ascorbic acid | 0.4 |
| EDTA | 0.2 |
| Sodium hydroxide 30% | 1.0 |
| Aqua ad | 100.0 |

The lightening composition comprises much more sodium glycinate than described in DE 19527121 A1, it is thus critical to the stability of a cosmetic composition. The cosmetic composition remains stable over three months at each: 5° C., 25° C. and 50° C. storage temperature. A composition is considered stable when no phase separation into two or more phases is observed.

The lightening composition of example 8 (according to table 4) was mixed in 1:1 ratio with developer composition 1 or 2 (according table 1) and applied onto human hair with shade 7/0. After remaining on the hair for 30 minutes, the hair was rinsed with water ($T_{water}=30°$ C.), washed with a neutral shampoo ($T_{water}=30°$ C.) and dried. L*a*b* values were determined prior and after the treatment (see Table 5).

TABLE 5

|  | L* | a* | b* | ΔE |
|---|---|---|---|---|
| Human hair, shade 7/0 | 30.33 | 6.56 | 10.98 |  |
| treated with lightening composition and developer composition 1, ratio 1:1 | 35.57 | 7.77 | 14.06 | 6.20 |
| treated with lightening composition and developer composition 2, ratio 1:1 | 36.19 | 8.41 | 15.43 | 7.59 |

The difference in L*-values between human hair prior to and after the treatment is a measure of the lightening effect caused by treatment with the composition used in the present example.
The lightening effect caused by the treatment is more than 5 units (ΔL* = 35.57-30.33 = 5.23 and ΔL* = 36.19-30.33 = 5.86). This is comparable with the degree of lightening which can be achieved with conventional ammonia based lightening compositions (e.g.: Koleston Perfect 12/0 of Wella, 65824 Schwalbach, Germany).

Example 9: Process for the Manufacturing of a Cream-Like Cosmetic Coloring Composition The following process represents one example in which Glycine was the selected amino acid.

Step 1:

With stirring, xanthan gum (4.0 g) was dissolved in water (220.4 g) at ambient temperature. To the obtained solution Crodafos CES (60.0 g) and Ceteareth-25 (4.0 g), Stearyl alcohol (20.0 g), Cetearyl alcohol 50:50 (30.0 g), a mixture of Lauryl alcohol and Myristyl alcohol 70:30 (40.0 g) followed by the addition of sodium hydroxide 30% in water (8.0 g). Then tris(hydroxymethyl)aminomethane (50.0 g) is added and the slurry was heated to 75-80° C., homogenized and then allowed to cool to 50° C. Weight: 436.4 g.

Step 2:

In a separate beaker water (220.0 g) was placed. Stirring was started and sodium hydroxide 30% in water (213.6 g), and Glycine (120.0 g) were added, then disodium EDTA (2.0 g), ascorbic acid (4.0 g), sodium sulfite (3.0 g). If the composition contains one or more dyes, the amount of dyes was compensated for by reducing the amount of water to the same extent. Weight: 563.6 g In the following table a typical example is given for Step 2 for illustration purposes.

| Aqua | 203.0 g |
|---|---|
| Sodium hydroxide, 30% in water | 213.6 g |
| Glycine | 120.0 g |
| Ascorbic acid | 4.0 g |
| Sodium sulfite | 3.0 g |
| Disodium-EDTA | 2.0 g |
| 1-Hydroxyethyl-4,5-diamino pyrazole sulfate | 6.0 g |
| p-Aminophenol | 2.0 g |
| Toluene-2,5-diamine sulfate | 1.0 g |
| m-Aminophenol | 9.0 g |
| Total weight of Step 2 | 563.6 g |

Step 3:

While stirring, the solution from step 2 was added to the dispersion of step 1. Then the obtained mixture was maintained at 40° C. for 10 minutes, whereby the mixture was homogenized again to obtain the tint composition. Total weight: 1000 g.

After further cooling to room temperature (e.g. 20-25° C.), the resulting cream was filled into tubes.

Example 10: Field Test

Various color shades of the inventive composition were evaluated in more than 30 salon tests. Tests were carried out as half-head tests vs. established color brands for direct comparison. One half of each model's hair (e.g. left side) was treated with a reference coloring composition and the other half of the hair (e.g. right side) was treated with a cosmetic coloring composition of the invention. The developer compositions of the reference brands were used according to the instructions for use; the peroxide strength of the inventive composition was identical to the hydrogen peroxide strength of the reference.

The tests comprised handling all steps of a color treatment in a salon, starting from the preparation of the ready-to-use composition, application to the hair and the on-head properties, removal of the cream from the hair after processing, and finally the dye performance.

Besides natural shades which are normally based on benzoaromatic dyes, fashioned shades comprising the heterocyclic 1-Hydroxyethyl-4,5-diamino pyrazole sulfate, which is known for its pronounced activity and dye performance, were also evaluated. The tested parameters and properties are considered of importance for professional use. In Table 6, scoring was in accordance with the criteria:

1 very poor, arduous 2 poor, laborious, tedious 3 average 4 good, easy 5 very good, very easy

TABLE 6

|  | Koleston Perfect Ammonium hydroxide | | INOA Monoethanolamine | | Invention Tris(hydroxymethyl)-amino-methane/ Glycine | |
|---|---|---|---|---|---|---|
| Alkalizer | Evaluation by hairdressers | Scoring | Evaluation by hairdressers | Scoring | Evaluation by hairdressers | Scoring |
| Extrusion of the tint | arduous due to compact cream consistency | 1 | easy | 4 | easy | 4 |

TABLE 6-continued

| Alkalizer | Koleston Perfect Ammonium hydroxide | | INOA Monoethanolamine | | Invention Tris(hydroxymethyl)-amino-methane/ Glycine | |
|---|---|---|---|---|---|---|
| | Evaluation by hairdressers | Scoring | Evaluation by hairdressers | Scoring | Evaluation by hairdressers | Scoring |
| Mixing with developer | laborious | 2 | easy | 4 | very easy | 5 |
| Application | tedious due to stickiness | 2 | easy | 4 | very easy | 5 |
| On head dilution with water and even distribution to lengths and tips | tedious due to cream stickiness | 2 | average | 3 | very easy | 5 |
| Rinsing after processing | tedious due to cream stickiness | 2 | very poor (1) | 1 | shampoo-like, very easy | 5 |
| Hair condition after rinsing | poor | 2 | good | 4 | very good | 5 |
| Softness of the hair | average | 3 | good | 4 | very soft | 5 |
| Hair condition after application of a mask | good | 4 | very good | 5 | very good | 5 |
| Care effect after shampooing 3x | average | 3 | noticeable | 4 | noticeable | 4 |
| Lift, lightening | very good | 5 | good | 4 | good | 4 |
| Grey coverage | very good | 5 | very good | 5 | very good | 5 |
| Root-to-tip evenness, natural shades | very good | 5 | very good | 5 | very good | 5 |
| Look of the coloration | "bold" | 2 | very natural | 5 | very natural | 5 |
| Root-to-tip evenness, fashioned shades (2) | lengths and tips of longer hair noticeably more intense than the root part | 4 | not available, not rated | —/— | perfectly even | 5 |
| Overall points | | 42 | | 52 | | 67 |
| Rating (overall points/ number of tests) | | 3.0 | | 4.0 | | 4.8 |

(1): specific shampoo required
(2): shades comprising 1-Hydroxyethyl-4,5-diamino pyrazole sulfate Koleston Perfect is a trademark of Wella, INOA of L'Oreal. The applicability of all Koleston Perfect- and all INOA-product is similar to that shown in the table.

Tests were performed via blind testing using visual, sensorial and haptic examination by an experienced, professional hairdresser. All of these tests were performed by the same individual, under similar ambient conditions and in direct comparison (at the same time).

Test Methods

Tests no. 1-7 and 9 were performed via blind testing using visual, sensorial and haptic examination by an experienced, professional hairdresser. All of these tests were performed by the same individual, under similar ambient conditions and in direct comparison (at the same time).

Test No. 8: Delta E (ΔE)

Colorimetric measurements were made before and after the treatment of the hair, using a Konica Minolta Chroma Meter CR-200 in the L*a*b*-system. According to this system, L* indicates the brightness of the color (0 yields black and 100 indicates white). The chromaticity coordinates are expressed by the parameters a* and b*. The a* axis extends from green (−a) to red (+a) and the b* axis from blue (−b) to yellow (+b).

The change of color, lightening and/or coloring, is represented by the difference of color ΔE between the hair before and after the treatment. A high value indicates a high change in color. ΔE corresponds to the equation $$\Delta E = [(L_1 - L_0)^2 + (a_1 - a_0)^2 + (b_1 - b_0)^2]^{1/2}$$

wherein the index 0 stands for a sample before the treatment and the index 1 for a sample after the treatment.

REFERENCE NUMERALS (1) head
(2) (virtual) line between left side and right side of head
L left side of head
R right side of head

The invention claimed is:

1. A cosmetic composition, comprising at least these components:
   a. tris(hydroxymethyl)aminomethane;
   b. at least one amino acid;
   c. at least one organic phosphate ester compound selected from
      c1. monoester of phosphates of alkoxylated fatty alcohols,
         wherein the alkoxylated fatty alcohols are composed of C12-C22 fatty alcohols alkoxylated with from 1 to 50 moles of an alkylene oxide, the number of moles of alkylene oxide with respect to the moles of fatty alcohol;
      c2. diester of phosphates of non-alkoxylated fatty alcohols,
         wherein the non-alkoxylated fatty alcohols are composed of C12-C22 fatty alcohols; and
      c3. mixtures of c1 and c2;
   d. water;
   with the proviso that the composition does not comprise ammonia, salts of ammonia or a source of peroxy monocarbonate;
   wherein the composition further comprises a dye, which is selected from (a) at least one primary intermediate;
(b) at least one direct dye; and
(c) mixtures of (a) and (b).

2. The cosmetic composition according to claim 1, wherein the amino acid is selected from the group consisting of arginine, glycine, lysine, alanine, glutamine, histidine and serine.

3. The cosmetic composition according to claim 1, wherein the at least one organic phosphate ester compound is selected from the group consisting of dicetyl phosphate, ceteth-10 phosphate, oleth-5 phosphate and dioleyl phosphate.

4. The cosmetic composition according to claim 1, wherein the composition comprises from 1 to 10 wt. % of tris(hydroxymethyl)aminomethane, based on the total weight of the composition.

5. The cosmetic composition according to claim 1, wherein the composition comprises from 1.0 to 30 wt. % in total of one or more amino acids, based on the total weight of the composition.

6. The cosmetic composition according to claim 1, wherein the composition comprises from 0.1 to 6 wt. % in total of one or more organic phosphate ester compounds, based on the total weight of the composition.

7. The cosmetic composition according to claim 1, wherein the composition comprises from 0.1 to 8 wt. % in total of one or more dyes, based on the total weight of the composition.

8. The cosmetic composition according to claim 1, wherein the composition further comprises at least one non-ionic surfactant.

9. The cosmetic composition according to claim 1, wherein the at least one primary intermediate is 1,4-diamino-2-methoxymethyl-benzene.

10. A process of manufacturing a dispersion, wherein the dispersion comprises a cosmetic composition according to claim 1, wherein the process comprises at least these steps:
   i. providing water;
   ii. providing the at least one organic phosphate ester compound;
   iii. mixing the compounds provided in step i. to ii., further adding an inorganic base until a pH in the range of from 8 to 12 is reached;
   iv. providing tris(hydroxymethyl)aminomethane;
   v. applying heat to the mixture obtained from step iv. to achieve a temperature of 85° C. and maintaining this temperature for at least 10 minutes;
   vi. cooling the mixture to 50° C., thereby creating a mixture I;
   vii. adding to the mixture I an aqueous mixture II which aqueous mixture II comprises at least one amino acid and the at least one dye, whereby the pH of the aqueous mixture II is adjusted to a pH in the range of from 8 to 12, thereby creating a mixture III;
   viii. cooling the resulting mixture III to 40° C. and homogenizing, followed by cooling to room temperature
   whereby the dispersion is obtained.

11. A kit for coloring keratin fibers, comprising in individually packaged form at least two kit components:
   I. a cosmetic composition as claimed in claim 1;
   II. a developer composition comprising an oxidizing agent.

12. The kit according to claim 11, wherein the oxidizing agent comprises an aqueous solution of hydrogen peroxide.

13. A ready-to-use composition obtainable by mixing the kit components according to claim 11.

14. The ready-to-use composition according to claim 13, wherein the ratio of the cosmetic composition and the developer composition is in the range of from 1:1 and 1:3, each number based on parts by weight.

15. A process for coloring keratin fibers, comprising the steps of:
   I. providing keratin fibers;
   II. contacting the keratin fibers of step I. with the ready-to-use composition according to claim 13 and allowing the ready-to-use composition to remain on the keratin fibers for a period of time;
   III. optionally rinsing the keratin fibers;
   IV. optionally drying the keratin fibers.

16. A kit for coloring keratin fibers, comprising in individually packaged form at least two kit components:
   I. a dispersion obtainable by a process according to claim 10;
   II. a developer composition comprising an oxidizing agent.

17. The cosmetic composition according to claim 8, wherein the at least one non-ionic surfactant is present in an amount of 1-8 wt. %, based on the total weight of the composition.

18. The process of claim 10, wherein the inorganic base is added until a pH in the range of from 10 to 11 is reached.

19. The process of claim 10, wherein the pH of mixture II is adjusted in step vii. to a pH in the range of from 10 to 11.

* * * * *